United States Patent [19]
Harpe et al.

[11] Patent Number: 5,905,075
[45] Date of Patent: May 18, 1999

[54] CHROMIUM NICOTINATE COMPOSITIONS AND USES THEREOF

[75] Inventors: Jon de la Harpe, New York; Fredric D. Price, Bedford; Lawrence W. Chakrin, Chatham, all of N.Y.; James R. Komorowski, Stratford, Conn.; Lauren K. Skluth, Goldens Bridge, N.Y.

[73] Assignee: AMBI Inc., Purchase, N.Y.

[21] Appl. No.: 09/143,256

[22] Filed: Aug. 28, 1998

[51] Int. Cl.$^6$ .......................... A61K 31/555; A61K 31/44
[52] U.S. Cl. ............................................. 514/188; 514/356
[58] Field of Search ...................... 514/188, 356

[56] References Cited

U.S. PATENT DOCUMENTS

| | | | |
|---|---|---|---|
| Re. 33,988 | 7/1992 | Evans | 514/188 |
| 4,954,492 | 9/1990 | Jensen | 514/188 |
| 5,087,623 | 2/1992 | Boynton et al. | 514/188 |
| 5,087,624 | 2/1992 | Boynton et al. | 514/188 |
| 5,175,156 | 12/1992 | Boynton et al. | 514/188 |
| 5,194,615 | 3/1993 | Jensen | 546/5 |

FOREIGN PATENT DOCUMENTS

WO 96/35421  11/1996  WIPO .

OTHER PUBLICATIONS

Boyle, et al., *Chromium Depletion n the Pathogenesis of Diabetes and Atherosclerosis*, Southern Medical Journal 70(12):1449–1453, 1977.

Carstensen,, J.T., *Pharmaceutical Principles of Solid Dosage Forms*, Technonic Publishing Co., Inc., Lancaster, PA, pp.228–230, 1993.

Kamath, et al., *Absorption, Retention and Urinary Excretion of Chromium–51 in Rats Pretreated with Indomethacin and Dosed with Dimethylprostaglandin $E_2$, Misoprostol of Prostacyclin*[1,2,3], J. Nutrition 127:478–482, 1997.

Singh, et al., *Pharmacology of an extract of salai guggal ex–Boswellia serrata, a new non–steroidal anti–inflammatory agent*, Agents and Actions 18:407–412, 1986.

*Coated Pharmaceutical Dosage Forms: Fundamentals, Manufacturing Techniques, Biopharmaceutical Aspects, Test Methods and Raw Materials*, CRC Press, Washington, DC, 1998.

*Recommended Daily Allowances*, Ninth Revised Edition, The national Academy of Sciences, p. 160, 1980.

*Primary Examiner*—Raymond Henley, III
*Attorney, Agent, or Firm*—Knobbe, Martens, Olson & Bear, LLP

[57] ABSTRACT

Compositions comprising chromic tripicolinate or chromic polynicotinate in combination with nicotinic acid, picolinic acid or both nicotinic acid and picolinic acid. The compositions may further comprise at least one of a cyclooxygenase inhibitor, an acid and a mucolytic. The compositions are useful for supplementing dietary chromium, lowering blood glucose levels, lowering serum lipid levels and increasing lean body mass.

35 Claims, No Drawings

CHROMIUM NICOTINATE COMPOSITIONS AND USES THEREOF

FIELD OF THE INVENTION

The present invention relates to compositions comprising chromic tripicolinate or chromic polynicotinate in combination with picolinic acid, nicotinic acid or both picolinic and nicotinic acids, and uses of these compositions in lowering blood glucose levels, increasing lean body mass and lowering blood serum lipid levels.

Background of the Invention

Chromium is a nutritionally essential trace element. The essentiality of chromium in the diet was established in 1959 by Schwartz, as cited in Present Knowledge in Nutrition, page 571, fifth edition (1984, the Nutrition Foundation, Washington, DC). Chromium depletion is characterized by the disturbance of glucose, lipid and protein metabolism and by a shortened lifespan. Chromium is essential for optimal insulin activity in all known insulin-dependent systems (Boyle et al., Southern Med. J 70:1449–1453, 1977). Insufficient dietary chromium has been linked to both maturity-onset diabetes and to cardiovascular disease.

The principle energy sources for the body are glucose and fatty acids. Chromium depletion results in biologically ineffective insulin and compromised glucose metabolism. Under these conditions, the body must rely primarily on lipid metabolism to meet its energy requirements, resulting in the production of excessive amounts of acetyl-CoA and ketone bodies. Some of the documented acetyl-CoA is converted to increased cholesterol biosynthesis, resulting in hypercholesterolemia. Diabetes mellitus is characterized in large part by glycosuria, hypercholesterolemia, and often ketoacidosis. The accelerated atherosclerotic process seen in diabetics is associated with hypercholesterolemia (Boyle et al., supra.).

Dietary supplementation of chromium to normal individuals has been reported to lead to improvements in glucose tolerance, serum lipid concentrations, including high-density lipoprotein cholesterol, insulin and insulin binding (Anderson, Clin. Psycho. Biochem. 4:31–41, 1986). Supplemental chromium in the trivalent form, e.g. chromic chloride, is associated with improvements of risk factors associated with adult-onset (Type II) diabetes and cardiovascular disease.

Chromium functions as a cofactor for insulin. It binds to the insulin receptor and potentiates many, and perhaps all, of its functions (Boyle et al., supra.). These functions include, but are not limited to, the regulation of carbohydrate and lipid metabolism. (Present Knowledge in Nutrition, supra, at p. 573–577). The introduction of inorganic chromium compounds per se into individuals is not particularly beneficial. Chromium must be converted endogenously into an organic complex or must be consumed as a biologically active molecule. Only about 0.5% of ingested inorganic chromium is assimilated into the body (Recommended Daily Allowances, Ninth Revised Edition, The National Academy of Sciences, page 160, 1980). Only 1–2% of most organic chromium compounds is assimilated into the body.

U.S. Pat. No. Re. 33,988 discloses that when selected essential metals, including chromium, are administered to mammals as exogenously synthesized coordination complexes of picolinic acid, they are directly available for absorption without competition from other metals. This patent describes a composition and method for selectively supplementing the essential metals in the human diet and for facilitating absorption of these metals by intestinal cells. These complexes are safe, inexpensive, biocompatible and easy to produce. These exogenously synthesized essential metal coordination complexes of picolinic acid (pyridine-2-carboxylic acid) have the following structural formula:

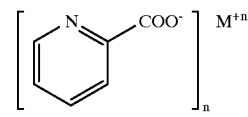

wherein M represents the metallic cation and n is equal to the cation's valence. For example, when M is Cr and n=3, then the compound is chromic tripicolinate. Other chromium picolinates disclosed include chromic monopicolinate and chromic dipicolinate.

The U.S. Recommended Daily Intake (RDI) of chromium is 120 $\mu$g. U.S. Pat. No. 5,087,623, the entire contents of which are hereby incorporated by reference, describes the administration of chromic tripicolinate for the treatment of adult-onset diabetes in doses ranging from 50 to 500 $\mu$g. International Patent Application No. WO96/35421 discloses the use of high doses of chromic tripicolinate (providing 1,000–10,000 $\mu$g chromium/day) for reducing hyperglycemia and stabilizing the level of serum glucose in humans with Type II diabetes. Allowed U.S. patent application Ser. No. 08/908,819 discloses a chromic tripicolinate-biotin composition and its use in lowering blood glucose levels in humans with Type II diabetes.

U.S. Pat. Nos. 5,087,623; 5,087,624; and 5,175,156, the entire contents of which are hereby incorporated by reference, disclose the use of chromium tripicolinate for supplementing dietary chromium, reducing hyperglycemia and stabilizing serum glucose, increasing lean body mass and reducing body fat, and controlling blood serum lipid levels, including the lowering of undesirably high blood serum LDL-cholesterol levels and the raising of blood serum HDL-cholesterol levels. U.S. Pat. Nos. 4,954,492 and 5,194,615, the entire contents of which are hereby incorporated by reference, describe a related complex, chromic nicotinate, which is also used for supplementing dietary chromium and lowering serum lipid levels. Picolinic acid and nicotinic acid are position isomers having the following structures:

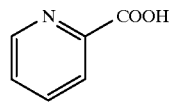 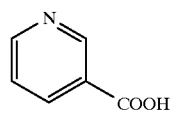

picolinic acid      nicotinic acid

Nicotinic acid and picolinic acid form coordination complexes with monovalent, divalent and trivalent metal ions and facilitate the absorption of these metals by transporting them across intestinal cells and into the bloodstream. Chromium absorption in rats following oral administration of $CrCl_3$ was facilitated by the non-steroidal anti-inflammatory drugs (NSAIDs) aspirin and indomethacin (Davis et al., J Nutrition Res. 15:202–210, 1995; Kamath et al., J. Nutrition 127:478–482, 1997). These drugs inhibit the enzyme cyclooxygenase which converts arachidonic acid to various prostaglandins, resulting in inhibition of intestinal mucus formation and lowering of intestinal pH which facilitates chromium absorption.

The present invention provides improved chromic tripicolinate and chromic polynicotinate compositions which facilitate absorption of chromium and other endogenous or exogenous metals, for use in lowering blood glucose levels, serum lipid levels and increasing lean body mass.

SUMMARY OF THE INVENTION

One embodiment of the present invention is a composition for supplementing dietary chromium and facilitating absorption of essential metals, the composition comprising chromic polynicotinate in combination with picolinic acid, nicotinic acid or both picolinic acid and nicotinic acid. In one aspect of this preferred embodiment, the composition is incorporated into a pharmaceutically acceptable carrier. Preferably, the carrier is a tablet, capsule, microbead, emulsion, powder, granule, suspension, syrup or elixir. Advantageously, the microbead is a sugar beadlet or microcrystalline cellulose beadlet and the chromic polynicotinate and picolinic acid, nicotinic acid or picolinic acid/nicotinic acid are coated on the beadlet. In one aspect of this preferred embodiment, the chromic nicotiinate and picolinic acid, nicotinic acid or picolinic acid/nicotinic acid are in a ratio of between about 1:10 and about 10:1 (w/w). The composition may further comprise at least one of a cyclooxygenase inhibitor, an acid, a mucolytic, and a salicin-containing herb. Preferably, the tablet or capsule is coated with an enteric coating.

The present invention also provides a method for supplementing dietary chromium in an individual, comprising orally administering to the individual chromic polynicotinate in combination with picolinic acid, nicotinic acid or both picolinic acid and nicotinic acid. Preferably, the chromic polynicotinate and picolinic acid, nicotinic acid or picolinic acid/nicotinic acid are incorporated in a pharmaceutically acceptable carrier. Advantageously, the pharmaceutically acceptable carrier is a tablet, capsule, microbead, emulsion, powder, granule, suspension, syrup or elixir. The composition may further comprise at least one of a cyclooxygenase inhibitor, an acid, a mucolytic, and a salicin-containing herb. Preferably, the tablet or capsule is coated with an enteric coating. In one aspect of this preferred embodiment, the microbead is a sugar beadlet or microcrystalline cellulose beadlet and the chromic tripicolinate and picolinic acid, nicotinic acid or picolinic acid/nicotinic acid are coated on the beadlet. Advantageously, the effective amount is between about 50 and about 10,000 micrograms.

Another embodiment of the present invention is a method for reducing hyperglycemia and stabilizing serum glucose levels in an individual in need thereof, comprising orally administering to the individual an effective daily hyperglycemia-reducing amount of chromic polynicotinate in combination with picolinic acid, nicotinic acid, or both picolinic acid and nicotinic acid. Preferably, the chromic polynicotinate and picolinic acid, nicotinic acid or picolinic acid/nicotinic acid are incorporated in a pharmaceutically acceptable carrier. Advantageously, the pharmaceutically acceptable carrier is a tablet, capsule, microbead, emulsion, powder, granule, suspension, syrup or elixir. The composition may further comprise at least one of a cyclooxygenase inhibitor, an acid, a mucolytic, and a salicin-containing herb. Preferably, the tablet or capsule is coated with an enteric coating. In one aspect of this preferred embodiment, the microbead is a sugar beadlet or microcrystalline cellulose beadlet and the chromic polynicotinate and the picolinic acid, nicotinic acid or picolinic acid/nicotinic acid are coated on said beadlet. In another aspect of this preferred embodiment, the microbead is microcrystalline cellulose and the chromium polynicotinate and picolinic acid, nicotinic acid or picolinic acid/nicotinic acid are coated onto the microcrystalline cellulose. Preferably, the chromic polynicotinate and picolinic acid, nicotinic acid or picolinic acid/ nicotinic acid are in a ratio of between about 1:10 and about 10:1 (w/w). Advantageously, the effective amount is between about 50 and about 10,000 micrograms.

The present invention also provides a method for increasing lean body mass and reducing body fat in an individual in need thereof, comprising orally administering to the individual an effective, lean body mass-increasing amount of chromic polynicotinate in combination with picolinic acid, nicotinic acid or both picolinic acid and nicotinic acid. Preferably, the chromic polynicotinate and picolinic acid, nicotinic acid or picolinic acid/nicotinic acid are incorporated in a pharmaceutically acceptable carrier. Advantageously, the pharmaceutically acceptable carrier is a tablet, capsule, microbead, emulsion, powder, granule, suspension, syrup or elixir. The composition may further include at least one of a cyclooxygenase inhibitor, an acid, a mucolytic, and a salicin-containing herb. Preferably, the tablet or capsule is coated with an enteric coating. In one aspect of this preferred embodiment, the microbead is a sugar beadlet or microcrystalline cellulose beadlet and the chromic tripicolinate and picolinic acid, nicotinic acid or picolinic acid/nicotinic acid are coated onto the beadlet. In another aspect of this preferred embodiment, the microbead is microcrystalline cellulose and the chromic polynicotinate and picolinic acid, nicotinic acid or picolinic acid/nicotinic acid are coated onto the microcrystalline cellulose. Preferably, the chromic polynicotinate and the picolinic acid, nicotinic acid or picolinic acid/nicotinic acid are in a ratio of between about 1:10 and about 10:1 (w/w). Advantageously, the effective amount is between about 50 and about 10,000 micrograms.

Another embodiment of the present invention is a method for reducing high levels of blood serum lipids in an individual in need thereof, comprising administering to the individual an effective blood serum lipid-reducing amount of chromic polynicotinate and picolinic acid, nicotinic acid or both picolinic acid and nicotinic acid. Preferably, the chromic polynicotinate and picolinic acid, nicotinic acid or picolinic acid/nicotinic acid are incorporated in a pharmaceutically acceptable carrier. Advantageously, the pharmaceutically acceptable carrier is a tablet, capsule, microbead, emulsion, powder, granule, suspension, syrup or elixir. The composition may further comprise at least one of a cyclooxygenase inhibitor, a mucolytic and a salicin-containing herb. Preferably, the tablet or capsule is coated with an enteric coating. In one aspect of this preferred embodiment, the microbead is a sugar beadlet or microcrystalline cellulose beadlet and the chromic polynicotinate and picolinic acid, nicotinic acid or picolinic acid/nicotinic acid are coated on the beadlet. In another aspect of this preferred embodiment, the microbead is microcrystalline cellulose and the chromic polynicotinate and picolinic acid, nicotinic acid or picolinic acid/nicotinic acid are coated onto the microcrystalline cellulose. Preferably, the chromic polynicotinate and picolinic acid, nicotinic acid or picolinic acid/nicotinic acid are in a ratio of between about 1:10 and about 10:1 (w/w). Advantageously, the effective amount is between about 50 and about 10,000 micrograms

DETAILED DESCRIPTION OF THE PREFERRED EMBODIMENTS

The present invention provides a composition comprising chromic tripicolinate or chromic polynicotinate in combination with picolinic acid, nicotinic acid or both picolinic acid and nicotinic acid. In a preferred embodiment, the chromic picolinate and chromic polynicotinate are synthetic.

The chromic tripicolinate and chromic polynicotinate facilitate absorption of chromium by intestinal cells, while the additional picolinic acid and/or nicotinic acid in the composition facilitates absorption of other ingested chromium as well as other metals including, but not limited to, copper, iron, magnesium, manganese and zinc. Thus, these compositions are readily absorbable forms of chromium which also facilitate absorption of other essential metals in the human diet. The chromic tripicolinate and chromic polynicotinate compositions of the invention have the same uses as described for chromic tripicolinate in U.S. Pat. Nos. 5,087,623, 5,087,624 and 5,174,156, namely supplementing dietary chromium, lowering blood glucose levels in diabetics, lowering serum lipid levels and increasing lean body mass.

The synthesis and use of chromium picolinates is described in U.S. Pat. Nos. Re33,988 and 5,087,623. Chromic tripicolinate is available from health food stores, drug stores and other commercial sources, including Nutrition 21 (San Diego, Calif.). The synthesis and use of chromic polynicotinate is described in U.S. Pat. No. 5,194,615. Picolinic acid and nicotinic acid are available from many commercial sources, including Sigma-Aldrich (St. Louis, Mo.) (picolinic acid; catalog No. P5503; nicotinic acid; catalog No. PN4126). The compositions of the present invention are prepared by incorporating the components into a pharmaceutically acceptable carrier, including but not limited to tablets, capsules and microbeads, preferably sugar beadlets or microcrystalline cellulose.

For oral administration, the chromic tripicolinate or chromic polynicotinate and nicotinic acid, picolinic acid or both nicotinic acid and picolinic acid may be incorporated into a tablet, aqueous or oil suspension, dispersible powder or granule, microbead, emulsion, hard or soft capsule, syrup or elixir. The components of the composition may also be administered separately. Compositions may be prepared according to any method known in the art for the manufacture of pharmaceutically acceptable compositions and such compositions may contain one or more of the following agents: sweeteners, flavoring agents, coloring agents and preservatives. Tablets containing the active ingredients in admixture with non-toxic pharmaceutically acceptable excipients suitable for tablet manufacture are acceptable. "Pharmaceutically acceptable" means that the agent should be acceptable in the sense of being compatible with the other ingredients of the formulation (as well as non-injurious to the individual). Such excipients include inert diluents such as calcium carbonate, sodium carbonate, lactose, calcium phosphate or sodium phosphate; granulating and disintegrating agents, such as corn starch and alginic acid; binding agents such as starch, gelatin or acacia; and lubricating agents such as magnesium stearate, stearic acid or talc. Tablets may be uncoated or may be coated with known techniques to delay disintegration and absorption in the gastrointestinal tract and thereby provide a sustained action over a longer period of time. For example, a time delay material such as glyceryl monostearate or glyceryl stearate alone or with a wax may be employed.

In another preferred embodiment, tablets, capsules or microbeads are coated with an enteric coating which prevents dissolution in the acidic environment of the stomach. Instead, this coating dissolves in the small intestine at a more neutral pH. Because chromic tripicolinate may be more stable at this neutral pH than at the acidic pH of the stomach, enhanced absorption occurs because the chromic tripicolinate remains substantially intact until it reaches the small intestine. Such enteric coated compositions are described by Bauer et al., Coated Pharmaceutical Dosage Forms: Fundamentals, Manufacturing Techniques, Biopharmaceutical Aspects, Test Methods and Raw Materials, CRC Press, Washington, DC, 1998, the entire contents of which are hereby incorporated by reference.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the chromic tripicolinate or polynicotinate complexes of the invention in admixture with excipients for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agent, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, may also be present.

Syrups and elixirs may be formulated with sweetening agents, such as glycerol, sorbitol or sucrose. Such formulations may also contain a demulcent, a preservative, a flavoring or a coloring agent.

The oral formulations described above may also include aspirin (acetylsalicylic acid), other salicylates, or another NSAID such as indomethacin, ibuprofen, acetaminophen, naproxen or any drug capable of inhibiting the cyclooxygenase pathway leading to prostaglandin synthesis. This results in a decrease in intestinal mucus production and lower intestinal pH which facilitates absorption of the chromic tripicolinate compositions of the present invention. The oral compositions may further include mucolytics such as guaifenesin and the like, to inhibit intestinal mucus production, and/or acids such as ascorbic acid, citric acid and the like to lower intestinal pH. Inclusion of one or both of these compounds further enhances chromium absorption. There are two forms of cyclooxygenase (cox), cox1 and cox2, which differ in their sensitivity to inhibition by NSAIDs. The cox2 isozyme promotes prostaglandin formation at sites of inflammation, but not at other sites such as the gastrointestinal tract. In contrast, relatively selective inhibition of cox1 facilitates chromic tripicolinate and chromic polynicotinate absorption. Although the selective inhibition of cox1 is desirable, any inhibitor or cox1 or cox2 can be formulated with the chromic tripicolinate and chromic polynicotinate compositions of the invention. Cox inhibitors, acids and mucolytics may also be coadministered with the chromic tripicolinate and chromic polynicotinate compositions of the invention. The amount of these drugs formulated with or coadministered with the chromic tripicolinate compositions of the invention are as follows: cox inhibitions, between about 50 mg and 500 mg; mucolytics, between about 10 mg and 250 mg; and acids, between about 50 mg and about 1,000 mg.

The coadministration or formulation of salicylate-containing herbs with the chromic tripicolinate and chromic polynicotinate compositions of the invention is also contemplated. Class I herbs, as documented in the American Herbal Products Association's Botanical Safety Handbook (herbs that can be safely consumed when used appropriately), such as *Boswelia serrata* (frankincense), *Betula lenta* (sweet birch), *Betula pubescens* (white birch), *Filipendula ulmaria* (meadowsweet), *Gaultheria procumbens* (wintergreens), *Populus balsamifera* and *Populus jackii* (balm of Gilead), and *Salix alba* (white willow) are all salicin-containing plants with salicylate-like properties. These herbs suppress prostaglandin synthesis by cox inhibition, thereby improving absorption of the chromic tripicolinate compositions of the invention. These herbs are relatively free from gastric ulcerogenic effects (Singh et al., Agents and Actions 18:407–412, 1986). In addition, pre-clinical acute toxicity studies have shown that salicin-containing plants do not cause hematological disturbances (American Herbal Products Association, Botanical Safety Handbook, 1997).

The compounds and herbs described above all effect gut physiology by inhibiting prostaglandin synthesis, decreasing mucus production, and lowering gastrointestinal pH. The inclusion of these compounds, as well as an enteric coating, into the oral chromic tripicolinate and chromic polynicotinate compositions of the invention results in a multicomponent delivery system which allows delivery of these agents to the gastrointestinal tract where they work in concert to facilitate chromic tripicolinate absorption.

In a preferred embodiment chromic tripicolinate or chromic polynicotinate, and picolinic acid, nicotinic acid or both nicotinic acid and picolinic acid, are coated onto microbeads. In a preferred embodiment, these microbeads are sugar beadlets of various sizes, also known as nonpareils, and are commercially available from, for example, Smith-Kline Beecham. If the microbeads are to be used to administer the compositions of the invention to diabetic patients, the administration of other types of microbeads, such as microcrystalline cellulose, is preferred. Microcrystalline cellulose is commercially available and can be processed into beadlets of various sizes by micronization, a technique well known in the art. The microbeads are essentially a carrier for the compositions of the invention. For a description of coated beadlets, see, for example, Carstensen, J. T., Pharmaceutical Principles of solid Dosage Forms, Technonic Publishing Co., Inc., Lancaster, Pa., pp. 228–230, 1993, hereby incorporated by reference. Aqueous solutions containing the chromic tripicolinate, chromic polynicotinate, nicotinic acid and picolinic acid components of the composition are sprayed onto the microbeads by well known methods, by suspending the inicrobeads in an upcurrent of air and introducing a fine spray of the active ingredients which form a coating on the outside of the microbeads which is then allowed to dry. The desired components (e.g. chromic tripicolinate and nicotinic acid; chromic trinicotinate and picolinic acid) may be combined into one same solution or applied using separate solutions. Optionally, the coated microbeads can be further coated with a substance to protect the active ingredients coated onto the beads, such as latex. The microbeads may be placed in a capsule prior to administration. In another preferred embodiment, the capsule or the microbeads are coated with an enteric coating to delay dissolution until reaching the small intestine.

Typically, the dosage range of chromium administered to an individual in the form of chromic tripicolinate/picolinic acid, chromic tripicolinate/nicotinic acid, chromic tripicolinate/picolinic acid/nicotinic acid, chromic polynicotinate/picolinic acid, chromic polynicotinate/nicotinic acid, chromic polynicotinate/picolinic acid/nicotinic acid provides between about 50 and 10,000 micrograms per day of chromium; preferably between about 100 and 1,000 micrograms per day; more preferably, between about 200 and 500 micrograms per day. In a preferred embodiment, the ratio of chromic tripicolinate or chromic polynicotinate to picolinic acid, nicotinic acid or picolinic acid/nicotinic acid ranges from about 10:1 to about 1:10 (w/w), more preferably from about 5:1 to about 1:5 (w/w).

It will be appreciated that although specific embodiments of the invention have been described herein for purposes of illustration, various modifications may be made without deviating from the spirit and scope of the invention. Accordingly, the invention is not limited except as by the appended claims.

What is claimed is:

1. A composition for supplementing dietary chromium and facilitating absorption of essential metals, said composition comprising chromic polynicotinate in combination with picolinic acid, nicotinic acid or both picolinic acid and nicotinic acid.

2. The composition of claim 1, wherein said composition is incorporated into a pharmaceutically acceptable carrier.

3. The composition of claim 2, wherein said carrier is selected from the group consisting of a tablet, capsule, microbead, emulsion, powder, granule, suspension, syrup and elixir.

4. The composition of claim 3, wherein said microbead is a sugar beadlet or microcrystalline cellulose beadlet and said chromic polynicotinate and said picolinic acid, nicotinic acid or picolinic acid/nicotinic acid are coated on said beadlet.

5. The composition of claim 1, wherein said chromic polynicotinate and said picolinic acid, nicotinic acid or picolinic acid/nicotinic acid are in a ratio of between about 1:10 and about 10:1 (w/w).

6. The composition of claim 1, further comprising at least one of a cyclooxygenase inhibitor, an acid, a mucolytic and a salicin-containing herb.

7. The composition of claim 3, wherein said tablet, capsule or microbeads are coated with an enteric coating.

8. A method for supplementing dietary chromium in an individual, comprising orally administering to said individual a composition comprising chromic polynicotinate in combination with picolinic acid, nicotinic acid or both picolinic acid and nicotinic acid.

9. The method of claim 8, wherein said chromic polynicotinate and picolinic acid, nicotinic acid or picolinic acid/nicotinic acid are incorporated into a pharmaceutically acceptable carrier.

10. The method of claim 9, wherein said pharmaceutically acceptable carrier is selected from the group consisting of a tablet, capsule, microbead, emulsion, powder, granule, suspension, syrup and elixir.

11. The method of claim 8, wherein said composition further comprises at least one of a cyclooxygenase inhibitor, an acid, a mucolytic and a salicin-containing herb.

12. The method of claim 10, wherein said tablet, capsule or microbeads are coated with an enteric coating.

13. The method of claim 10, wherein said microbead is a sugar beadlet or microcrystalline cellulose beadlet and said chromic polynicotinate and said picolinic acid, nicotinic acid or picolinic acid/nicotinic acid are coated on said beadlet.

14. The method of claim 8, wherein said effective amount is between about 50 and about 10,000 micrograms.

15. A method for reducing hyperglycemia and stabilizing serum glucose levels in an individual in need thereof, comprising orally administering to said individual an effective daily hyperglycemia-reducing amount of chromic polynicotinate in combination with picolinic acid, nicotinic acid or both picolinic acid and nicotinic acid.

16. The method of claim 15, wherein said chromic polynicotinate and picolinic acid, nicotinic acid or picolinic acid/nicotinic acid are incorporated into a pharmaceutically acceptable carrier.

17. The method of claim 16, wherein said pharmaceutically acceptable carrier is selected from the group consisting of a tablet, capsule, microbead, emulsion, powder, granule, suspension, syrup and elixir.

18. The method of claim 15, wherein said composition further comprises at least one of a cyclooxygenase inhibitor, an acid, a mucolytic and a salicin-containing herb.

19. The method of claim 17, wherein said tablet, capsule or microbeads are coated with an enteric coating.

20. The method of claim 17, wherein said microbead is a sugar beadlet or microcrystalline cellulose beadlet and said chromic polynicotinate and said picolinic acid, nicotinic acid or picolinic acid/nicotinic acid are coated on said beadlet.

21. The method of claim 15, wherein said effective amount is between about 50 and about 10,000 micrograms.

22. A method for increasing lean body mass and reducing body fat of an individual in need thereof, comprising orally administering to said individual an effective, lean body mass-increasing amount of chromic polynicotinate and picolinic acid, nicotinic acid or both picolinic acid and nicotinic acid.

23. The method of claim 22, wherein said chromic polynicotinate and picolinic acid, nicotinic acid or picolinic acid/nicotinic acid are incorporated into a pharmaceutically acceptable carrier.

24. The method of claim 23, wherein said pharmaceutically acceptable carrier is selected from the group consisting of a tablet, capsule, microbead, emulsion, powder, granule, suspension, syrup and elixir.

25. The method of claim 22, wherein said composition further comprises at least one of a cyclooxygenase inhibitor, an acid, a mucolytic and a salicin-containing herb.

26. The method of claim 24, wherein said tablet, capsule or microbeads are coated with an enteric coating.

27. The method of claim 24, wherein said microbead is a sugar beadlet or microcrystalline cellulose beadlet and said chromic polynicotinate and said picolinic acid, nicotinic acid or picolinic acid/nicotinic acid are coated on said beadlet.

28. The method of claim 22, wherein said effective amount is between about 50 and about 10,000 micrograms.

29. A method for reducing high levels of blood serum lipids in an individual in need thereof, comprising administering to said individual an effective blood serum lipid-reducing amount of chromic polynicotinate and picolinic acid, nicotinic acid or both picolinic acid and nicotinic acid.

30. The method of claim 29, wherein said chromic polynicotinate and picolinic acid, nicotinic acid or picolinic acid/nicotinic acid are incorporated into a pharmaceutically acceptable carrier.

31. The method of claim 30, wherein said pharmaceutically acceptable carrier is selected from the group consisting of a tablet, capsule, microbead, emulsion, powder, granule, suspension, syrup and elixir.

32. The method of claim 29, wherein said composition further comprises at least one of a cyclooxygenase inhibitor, an acid, a mucolytic and a salicin-containing herb.

33. The method of claim 31, wherein said tablet, capsule or microbeads are coated with an enteric coating.

34. The method of claim 31, wherein said microbead is a sugar beadlet or microcrystalline cellulose beadlet and said chromic polynicotinate and said picolinic acid, nicotinic acid or picolinic acid/nicotinic acid are coated on said beadlet.

35. The method of claim 29, wherein said effective amount is between about 50 and about 10,000 micrograms.

* * * * *